United States Patent
Drew

(10) Patent No.: US 10,500,366 B2
(45) Date of Patent: Dec. 10, 2019

(54) HUMIDIFICATION DEVICE

(71) Applicant: TELEFLEX MEDICAL INCORPORATED, Morrisville, NC (US)

(72) Inventor: Douglas Roy Drew, Raleigh, NC (US)

(73) Assignee: TELEFLEX MEDICAL INCORPORATED, Morrisville, NC (US)

(*) Notice: Subject to any disclaimer, the term of this patent is extended or adjusted under 35 U.S.C. 154(b) by 872 days.

(21) Appl. No.: 15/139,613

(22) Filed: Apr. 27, 2016

(65) Prior Publication Data

US 2016/0310692 A1   Oct. 27, 2016

Related U.S. Application Data

(60) Provisional application No. 62/153,034, filed on Apr. 27, 2015.

(51) Int. Cl.
*A61M 16/16*   (2006.01)
*A61M 16/10*   (2006.01)
(Continued)

(52) U.S. Cl.
CPC ........ *A61M 16/109* (2014.02); *A61M 11/041* (2013.01); *A61M 16/0833* (2014.02);
(Continued)

(58) Field of Classification Search
CPC ............ A61M 16/1075; A61M 16/108; A61M 16/1085
See application file for complete search history.

(56) References Cited

U.S. PATENT DOCUMENTS 4,621,632 A    11/1986  Bartels et al.
4,910,384 A *   3/1990  Silver .................. A61M 16/16
                                              128/203.17
(Continued)

FOREIGN PATENT DOCUMENTS

AU    2008202098 A1   2/2009
CN     204798549 U    11/2015
(Continued)

OTHER PUBLICATIONS

"Mu-Metal Alloy for Fabricated Shield," Magnetic MuMetal Shield Corp., p. 2-Typical Magnetic Properties, May 2014.

*Primary Examiner* — Timothy A Stanis
(74) *Attorney, Agent, or Firm* — Baker & Hostetler LLP

(57) ABSTRACT

A humidification device for a respiratory breathing circuit comprises an induction heater assembly to inject steam into a breathing circuit gas line. The assembly comprises a housing defining a housing lumen. An induction element is located around the housing lumen. A cannula is disposed within the housing lumen and surrounded by the induction element, the cannula being configured to receive a flow of water. A heating element is located inside the cannula, the heating element being at least partially surrounded by the induction element. The induction element is excited by electrical current to generate an oscillating magnetic field to create eddy currents in the heating element to heat the heating element, and thereby heat the flow of water in the cannula flowing past the heating element, to thereby vaporize the water into steam which exits the induction heater assembly and housing to be injected into the breathing circuit gas line.

16 Claims, 6 Drawing Sheets

(51) Int. Cl.
  *A61M 11/04* (2006.01)
  *A61M 16/08* (2006.01)
  *A61M 16/20* (2006.01)
(52) U.S. Cl.
  CPC ......... *A61M 16/16* (2013.01); *A61M 16/1095* (2014.02); *A61M 16/208* (2013.01); *A61M 2205/3606* (2013.01); *A61M 2205/368* (2013.01); *A61M 2205/3633* (2013.01); *A61M 2205/8262* (2013.01)

(56) References Cited

U.S. PATENT DOCUMENTS

| | | | |
|---|---|---|---|
| 5,222,185 A | | 6/1993 | McCord, Jr. |
| 5,286,942 A | | 2/1994 | McFadden et al. |
| 5,613,505 A | * | 3/1997 | Campbell ............. A24F 47/008 128/202.21 |
| 6,681,998 B2 | | 1/2004 | Sharpe et al. |
| 6,787,742 B2 | | 9/2004 | Kansa et al. |
| 6,802,314 B2 | | 10/2004 | McPhee |
| 6,918,389 B2 | | 7/2005 | Seakins et al. |
| 6,921,042 B1 | | 7/2005 | Goodzeit et al. |
| 6,923,179 B2 | | 8/2005 | Gupta et al. |
| 7,031,160 B2 | | 4/2006 | Tillotson |
| 7,938,113 B2 | | 5/2011 | Weinstein et al. |
| 8,052,127 B2 | | 11/2011 | Nichols et al. |
| 8,282,084 B2 | | 10/2012 | Nichols et al. |
| 8,327,845 B2 | | 12/2012 | Weinstein et al. |
| 8,662,479 B2 | | 3/2014 | Nichols et al. |
| 9,314,582 B2 | | 4/2016 | Korneff et al. |
| 2002/0078956 A1 | * | 6/2002 | Sharpe ................. A61M 11/042 128/203.26 |
| 2004/0102731 A1 | * | 5/2004 | Blackhurst ......... A61B 1/00154 604/26 |
| 2004/0151598 A1 | | 8/2004 | Young et al. |
| 2005/0095168 A1 | | 5/2005 | Centanni et al. |
| 2006/0012057 A1 | * | 1/2006 | Anthony ........... A61M 16/1075 261/154 |
| 2006/0047368 A1 | * | 3/2006 | Maharajh ................. F22B 1/28 700/283 |
| 2007/0277825 A1 | | 12/2007 | Bordewick et al. |
| 2008/0066751 A1 | | 3/2008 | Polacsek |
| 2008/0236577 A1 | | 10/2008 | Power et al. |
| 2009/0267242 A1 | | 10/2009 | Nichols et al. |
| 2010/0000980 A1 | * | 1/2010 | Popescu ................. A47J 36/20 219/201 |
| 2013/0081617 A1 | | 4/2013 | Cavendish |
| 2013/0112201 A1 | | 5/2013 | Graham et al. |
| 2013/0284165 A1 | | 10/2013 | Krimsky |
| 2013/0284169 A1 | | 10/2013 | Foote et al. |
| 2014/0373835 A1 | | 12/2014 | Ahmad et al. |
| 2015/0083126 A1 | * | 3/2015 | Rogers ................ A61M 16/026 128/203.14 |
| 2015/0352299 A1 | * | 12/2015 | Cortez, Jr. ........... A61M 11/041 128/200.23 |
| 2016/0001031 A1 | | 1/2016 | Laing et al. |
| 2016/0303342 A1 | | 10/2016 | Dwyer et al. |
| 2016/0310692 A1 | | 10/2016 | Drew |
| 2017/0266408 A1 | * | 9/2017 | Giovannelli ........ A61M 16/024 |

FOREIGN PATENT DOCUMENTS

| | | |
|---|---|---|
| DE | 4312793 A1 | 10/1994 |
| EP | 0 672 430 A2 | 9/1995 |
| EP | 2 269 680 A1 | 1/2011 |
| JP | 2018514301 A | 6/2018 |
| WO | 2007101298 A1 | 9/2007 |
| WO | 2009/015410 A1 | 2/2009 |
| WO | 2015196379 A1 | 12/2015 |
| WO | 2016036260 A1 | 3/2016 |

* cited by examiner

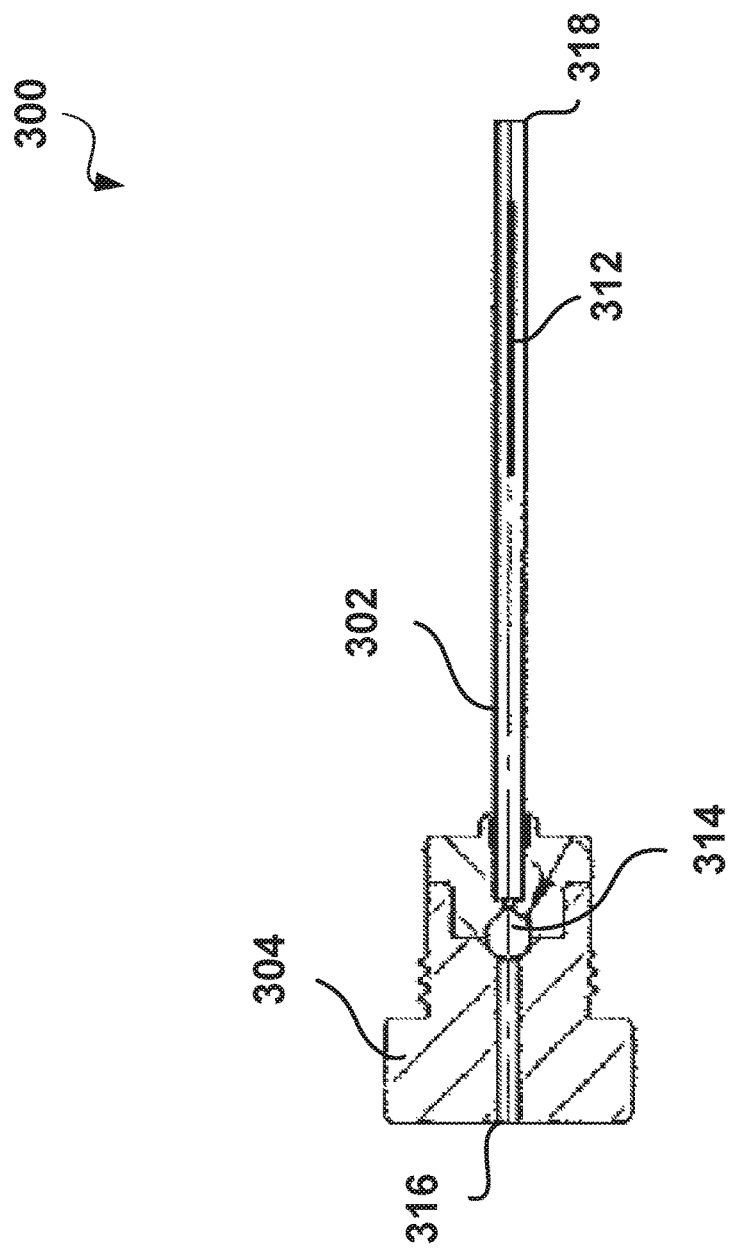

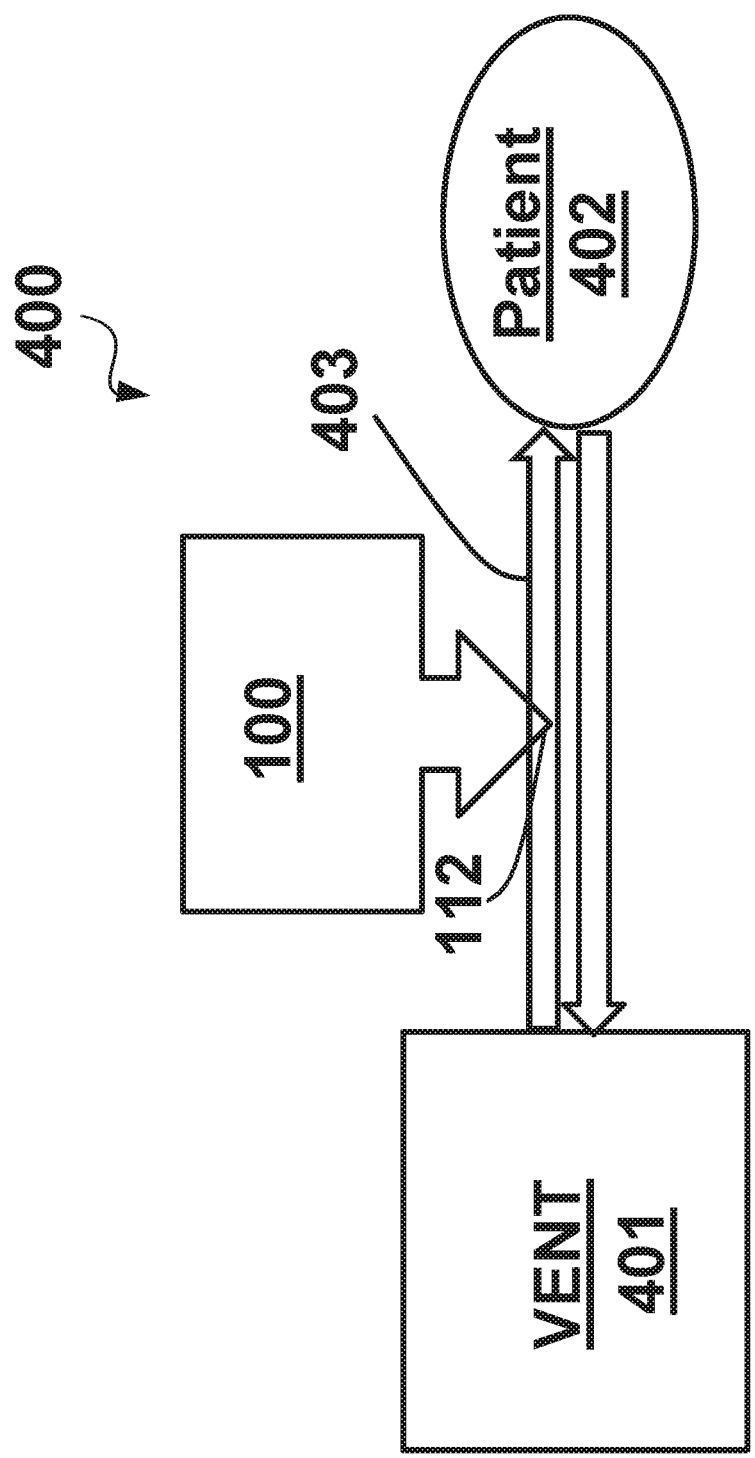

HUMIDIFICATION DEVICE

CROSS-REFERENCE TO RELATED APPLICATION

This application claims priority to U.S. provisional patent application No. 62/153,034, filed Apr. 27, 2015, the disclosure of which is incorporated by reference in its entirety.

FIELD OF THE INVENTION

The disclosure generally relates to a humidification device, and more particularly to a humidification device to provide on-demand heated humidification of gases within respiratory breathing circuits.

BACKGROUND

Humidification during mechanical ventilation is often necessary to reduce drying of a patient's airways and to prevent patient discomfort and possible complications such as inspissation of airway secretions, hypothermia, and atelectasis. While passive humidifiers can provide some relief, generally a heated humidifier is required to maintain proper temperature and moisture of air delivered to a patient.

Conventional methods for humidifying gas often utilize a water chamber. The water chamber holds a quantity of water that is heated using a heating element. Dry gas is fed into the chamber and is humidified with the heated water. The humidified gas then exits the chamber and is delivered to a breathing circuit connected to the patient. Unfortunately, these conventional heating elements can often be bulky and must be located away from patient. This arrangement can be cumbersome and can also lead to the formation of condensation in the breathing circuit.

Accordingly, there is a need for an improved humidification device that can provide on-demand humidification for respiratory breathing circuits.

SUMMARY OF THE INVENTION

The foregoing needs are met, to a great extent, by the humidification device described below.

In a first embodiment of the invention, a humidification device for a respiratory breathing circuit comprises an induction heater assembly configured to inject steam into a breathing circuit gas line of the respiratory breathing circuit. The assembly comprises a housing having a proximal end and a distal end, the housing defining a housing lumen extending from the proximal end to the distal end. An induction element is located around at least a portion of the housing lumen; and a power assembly is disposed in the housing for connection to a power source. A cannula having a proximal end and a distal end is disposed within the housing lumen and surrounded by the induction element, the cannula being configured to receive a flow of water. A heating element is located inside the cannula, the heating element being at least partially surrounded by the induction element. The induction element is configured to be excited by electrical current supplied from the power assembly, to generate an oscillating magnetic field to create eddy currents in the heating element to heat the heating element, and thereby heat the flow of water in the cannula flowing past the heating element, to thereby vaporize the water into steam which exits the induction heater assembly and housing to be injected into the breathing circuit gas line. In one embodiment, the heating element includes Mu-metal. In another embodiment, the heating element includes a magnetic material with a relative magnetic permeability greater than ten thousand. In another embodiment, the induction element comprises at least one helically wound metallic coil. In another embodiment, the induction element comprises one or more electrical conductors configured to generate an oscillating magnetic dipole. In another embodiment, the induction element comprises at least two electrical conductors configured to generate an oscillating magnetic multipole. In another embodiment, the at least two electrical conductors are wires or a printed circuit. In another embodiment, the induction heater assembly further comprises a thermal insulator located between the housing and the induction element. In another embodiment, the induction heater assembly further comprises a non-magnetic tube located within the housing lumen, the non-magnetic tube being disposed around the cannula.

In another aspect, the humidification device includes an induction heater assembly and a disposable assembly configured to be removably received in the induction heater assembly. The induction heater assembly includes a housing with a first proximal end and a first distal end. The housing defines a housing lumen that extends from the first proximal end to the first distal end. The induction heater assembly also includes an induction element located along at least a portion of the housing lumen and a power assembly connected to the housing. The disposable assembly includes a cannula with a second proximal end and a second distal end. The cannula is configured to be removably received within the housing lumen. The disposable assembly also includes a hub connected to the second proximal end of the cannula and a heating element located along the cannula.

In some aspects, the heating element can at least partially overlap with the induction element when the disposable assembly is removably received within the induction heater assembly. The heating element can be located along a distal portion of the cannula. The heating element can be made from a magnetic material with a relative magnetic permeability greater than one. The outer diameter of the hub can be greater than an inner diameter of the housing lumen. The induction element can include at least one helically wound metallic coil. Alternate configurations of the induction element can include at least two electrical conductors configured to generate an oscillating magnetic dipole. The induction element can also include at least two electrical conductors configured to generate an oscillating magnetic multipole. The electrical conductors may be wires or a printed circuit.

In some aspects, the hub of the disposable assembly can include an exposed positive thermocouple conductor and an exposed negative thermocouple conductor. The exposed positive thermocouple conductor and the exposed negative thermocouple conductor can each be configured to engage at least one corresponding thermocouple electrical contact formed on the housing when the disposable assembly is removably received in the induction heater assembly. At least one of the exposed positive thermocouple conductor and the exposed negative thermocouple conductor may be made from a magnetic material. In other aspects, the hub of the disposable assembly may include a first thermocouple conductor and the cannula may include a corresponding second thermocouple conductor, or the hub of the disposable assembly may include a first thermocouple conductor and a corresponding second thermocouple conductor may be located in a cannula lumen of the cannula.

In some aspects, the induction heater assembly can further include a thermal insulator located between the housing and the induction element. The induction heater assembly can further include a non-magnetic tube located within the housing lumen, where the non-magnetic tube can be configured to removably receive the cannula. The hub can include a check valve. The power assembly can be located at the first proximal end of the housing. The power assembly can be oriented along a power assembly axis that is at an acute angle relative to a central housing axis. The cannula can be made from a material selected from a metal, plastic, glass, ceramic, and a combination thereof. The hub can have a standardized Luer taper connection or a custom connection. The induction heater assembly can further include a plurality of cooling fins radially extending from an exterior surface of the housing. The induction heater assembly may also include a plurality of cooling fins extending into a gas flow line.

Certain aspects of the humidification device have been outlined such that the detailed description thereof herein may be better understood. There are, of course, additional aspects of the disclosure that will be described below. In this respect, before explaining at least one aspect of the humidification device in detail, it is to be understood that the humidification device is not limited in its application to the details of construction and to the arrangements of the components set forth in the following description or illustrated in the drawings. The humidification device is capable of aspects in addition to those described and of being practiced and carried out in various ways. Also, it is to be understood that the phraseology and terminology employed herein, as well as the Abstract, are for the purpose of description and is not be regarded as limiting.

As such, those skilled in the art will appreciate that the conception upon which this disclosure is based may readily be utilized as a basis for the designing of other structures, methods, and systems for carrying out the several purposes of the humidification device. It is important, therefore, that the claims be regarded as including such equivalent constructions insofar as they do not depart from the spirit and scope of the disclosure.

BRIEF DESCRIPTION OF THE DRAWINGS

In order that the disclosure may be readily understood, aspects of the humidification device are illustrated by way of examples in the accompanying drawings.

FIG. 5 is cross-sectional view of another implementation of a disposable assembly of a humidification device.

FIG. 6 is schematic system diagram of a humidification device of the invention coupled to a respiratory breathing circuit.

DETAILED DESCRIPTION

Figure 1:
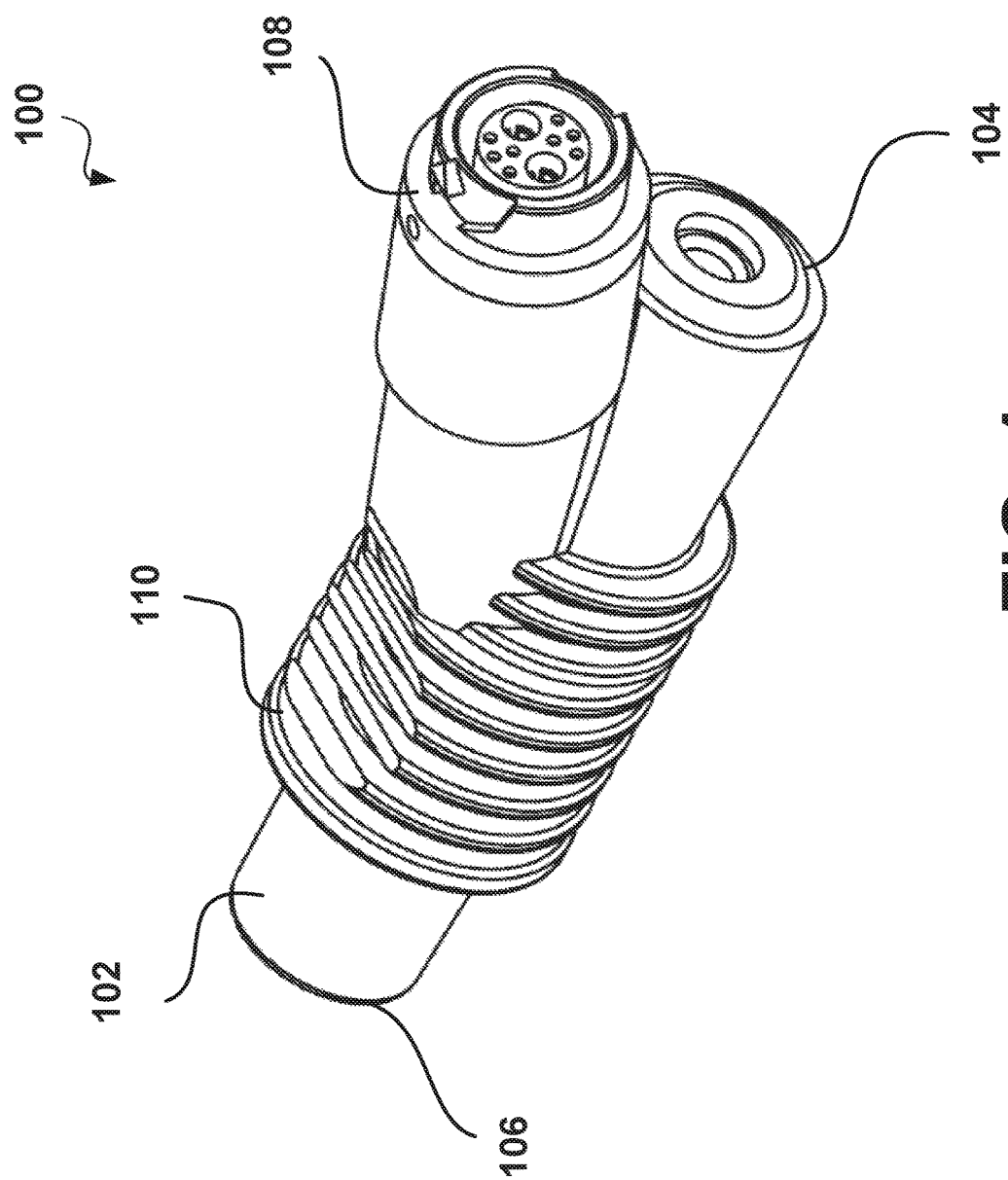
FIG. 1 is a perspective view of an induction heater assembly of a humidification device according to a first embodiment of the invention.

FIG. 1 illustrates an induction heater assembly 100 that forms part of a humidification device. The induction heater assembly 100 may include a housing 102 having a proximal end 104 and a distal end 106. The induction heater assembly 100 may also include a power and controls interface assembly 108 connected to the housing 102. A plurality of cooling fins 110 may extend from a portion of the housing 102 and the power and controls interface assembly 108. In some aspects, the cooling fins 110 may extend from a portion of the housing 102 and the power and controls interface assembly 108.

Figure 2:
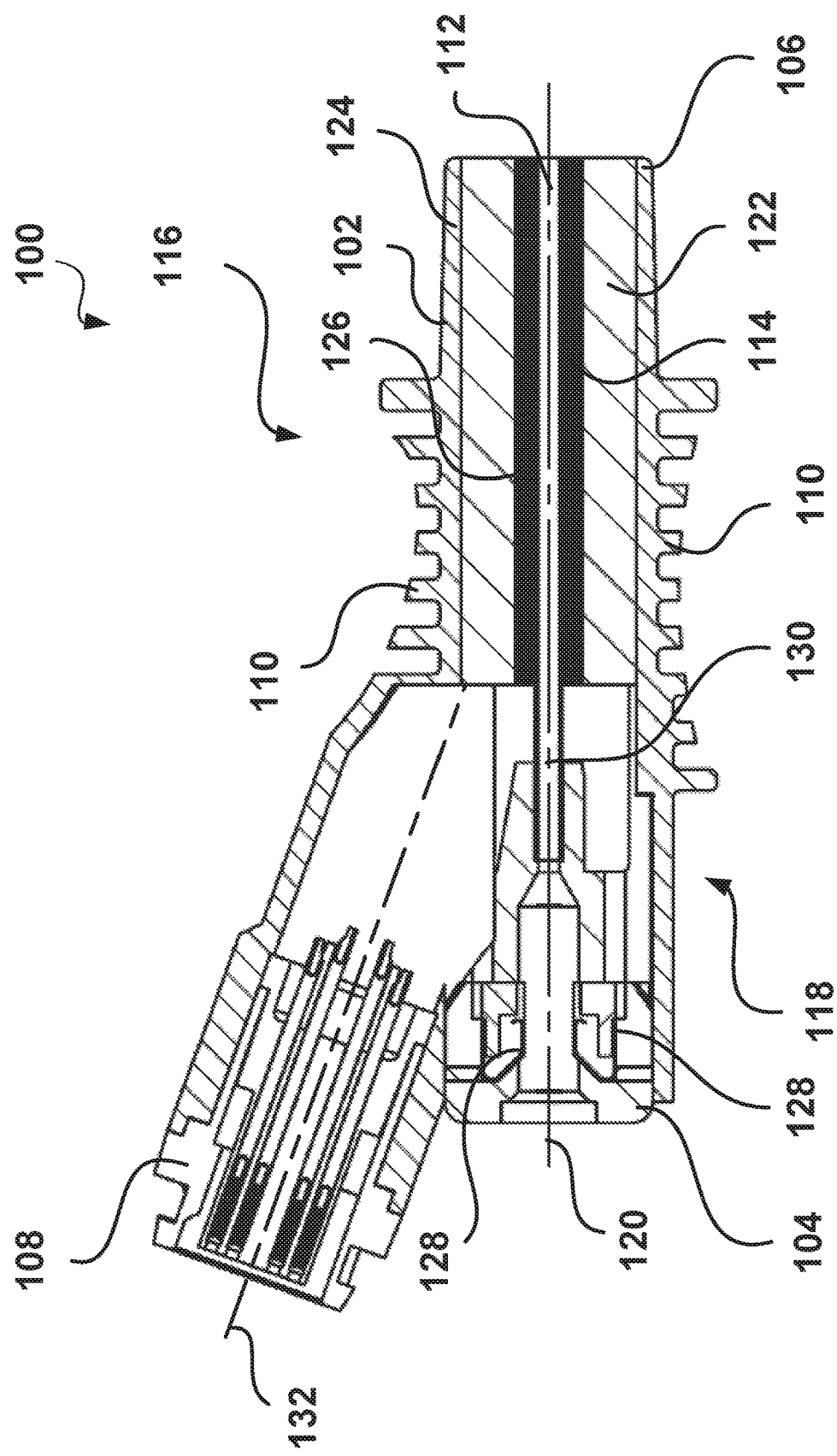
FIG. 2 is a cross-sectional view of the induction heater assembly of the humidification device of FIG. 1.

FIG. 2 illustrates a cross-sectional view of the induction heater assembly 100 of FIG. 1. The housing 102 may define a housing lumen 112. The housing lumen 112 may extend from the proximal end 104 to the distal end 106. The housing lumen 112 may be configured to receive a disposable assembly 200 (shown in FIG. 4) at the proximal end 104. The shape of the housing lumen 112 may match the shape of the disposable assembly 200. For example, the diameter of the housing lumen 112 may be greater towards the proximal end 104 than the diameter of the housing lumen 112 at the distal end.

The induction heater assembly 100 may include an induction element 114 located along the housing lumen 112. The induction element 114 may be located at a distal region 116 opposite from a proximal region 118 of the housing lumen 112. In other aspects, the induction element 114 may span from the distal region 116 to the proximal region 118 of the housing lumen 112. In some aspects, the induction element 114 may be an induction coil formed from a single or multiple enameled wires. If the induction element 114 is formed from multiple wires, the multiple wires may be twisted to form a Litz wire. A Litz wire configuration can reduce power loss and heat generated by the "skin effect" at high alternating current (AC) frequencies. The induction element 114 may be center-tapped, and a positive voltage may be supplied at the center tap. The ends of the induction element 114 may be alternately switched to ground to generate an oscillating magnetic field within the interior of the induction element 114. The oscillating magnetic field created from the induction element 114 may produce eddy currents to heat objects placed within the housing lumen 112.

In other aspects, the induction element 114 may be a pair of parallel electrical conductors configured to generate a dipole. The pair of parallel electrical conductors may extend within the housing lumen 112 parallel to a center axis 120. The pair of parallel electrical conductors may be insulated wires or conductive tracks formed onto a flexible printed circuit. The printed circuit may be formed to fit into the housing lumen 112 of the induction heater assembly 100. For example, in the aspect shown in FIG. 2, the induction element 114 as a printed circuit may be shaped like a hollow cylinder. To generate a dipole, a positive voltage may be supplied to one of the electrical conductors. The two ends of the other electrical conductor may be alternately switched to ground at a high frequency in order to generate an oscillating magnetic field within the housing lumen 112.

In further aspects, the induction element 114 may be more than two pairs of electrical conductors configured to generate an oscillating magnetic field having multiple poles, such as a quadrupole, hexapole, octupole, or another multipole system with either an even or odd number of magnetic poles. The pairs of electrical conductors may similarly extend within the housing lumen along the center axis 120. The electrical conductors may be insulated wires or conductive tracks formed onto a flexible printed circuit board. A positive voltage may be supplied to one set of electrical conductors. The set of electrical conductors may be alternately switched to ground at a high frequency to create a rapidly oscillating magnetic field. In other aspects, a circuit may be used to switch the polarity of each end of the induction element 114 to improve the efficiency of the induction element 114.

In the various aspects described above, the induction element 114 may generate an oscillating magnetic field with frequencies between 50-200 kHz. In some aspects, it may be desirable to have a range between 50-100 kHz, such as 50-60 kHz, 60-70 kHz, 70-80 kHz, 80-90 kHz, or 90-100 kHz. In other aspects, it may be desirable to have a range between 100-200 kHz, such as 100-150 kHz or 150-200 kHz. In further aspects, electromagnetic shielding, specifically radio frequency shielding, may be necessary such that the induction heater assembly 100 meets IEC 60601 EMI emission requirements.

As mentioned previously, a plurality of cooling fins 110 may extend from a portion of the housing 102. In other aspects, the cooling fins 110 may also extend from an exterior surface of the power and controls interface assembly 108. The cooling fins 110 may increase the rate of heat transfer from the induction heater assembly 100 by increasing the amount of surface area of the induction heater assembly 100 exposed to the air. In some aspects, the cooling fins 110 may be used to transfer heat from the induction element 114 into the gas flow stream by extending into the gas flow line. In some aspects, the cooling fins 110 may be made from the same material as the housing 102. In other aspects, the cooling fins may be made from material with a greater heat transfer coefficient than that of the material for the housing 102 in order to improve the cooling abilities of the cooling fins 110. The plurality of cooling fins 110 may have a circular, square, elliptical, rectangular, or other similar shape. The shape and size of the cooling fins 110 may be the same or may vary among the plurality of cooling fins 110.

The induction heater assembly 100 may also include a thermal insulator 122. The thermal insulator 122 may be located between the induction element 114 and the inner surface 124 of the housing 102. The thermal insulator 122 may extend radially from the outer surface 126 of the induction element 114. The thermal insulator 122 may be made from a material with low thermal conductivity to reduce heat transfer away from the induction element 114, which may increase the transfer of heat generating by the induction element 114 through the housing lumen 112 and cannula 202 into the fluid. Materials for the thermal insulator 122 may include ceramics, glass, composite materials such as glass-bonded mica (Mykroy/Mycalex), fiberglass, insulating plastics, or other suitable materials. The thermal insulator 122 may be formed from extruded tubing or another process suitable to shape the thermal insulator 122 to fit within the housing 102. Alternatively, a thermally conductive material may be selected for the thermal insulator 122 to transfer heat from the induction element 114 towards the cooling fins 110 and/or into the respiratory gas.

The induction heater assembly 100 may include thermocouple electrical contacts 128 formed on an inner surface 124 of the housing 102. The thermocouple electrical contacts 128 may be configured to engage corresponding thermocouple conductors (shown in FIG. 4) on the disposable assembly 200. The thermocouple electrical contacts 128 may be formed at the proximal region 118 of the housing 102. The thermocouple electrical contacts 128 may be in electrical connection with the power and controls interface assembly 108. Once the disposable assembly 200 is received within the induction heater assembly 100 and the thermocouple electrical contacts 128 engage the corresponding exposed thermocouple conductor surfaces 218 and 220, an electrical circuit will be completed within the induction heater assembly 100. In other aspects, the induction heater assembly 100 may use other devices, such as thermistors or resistance temperature detectors (RTDs), to measure temperature.

The induction heater assembly 100 may also include a non-magnetic tube 130 within and at the proximal region of the housing lumen 112. The non-magnetic tube 130 may only extend a portion of the length of the housing lumen 112. The non-magnetic tube 130 may be configured to receive the disposable assembly 200. The non-magnetic tube 130 may prevent direct contact between the induction element 114 and the disposable assembly 200 once the disposable assembly 200 is received within the induction heater assembly 100. The spacing between the induction element 114 and the disposable assembly 200 may improve performance of the induction element 114. The non-magnetic tube 130 may be made from plastic, glass such as borosilicate glass, ceramics, heat-resistant plastics, or other suitable non-magnetic materials.

As shown in FIG. 2, the power and controls interface assembly 108 is connected to the housing 102. The power and controls interface assembly 108 and housing 102 may be a single component. The power and controls interface assembly 108 may be implemented as a connector receptacle or other interface to facilitate a quick connection and/or disconnection with a power source and/or control interface. In other aspects, the power and controls interface assembly 108 may include a power source and be removably coupled to the housing 102. The power and controls interface assembly 108 may provide electrical power to the induction element 114 and/or thermocouple electrical contacts 128. The electrical connection may be established using insulated wires and/or flexible printed circuits. The power and controls interface assembly 108 may be oriented along a power assembly axis 132. In the aspect shown in FIG. 2, the power assembly axis 132 may be at an acute angle to the center axis 120 of the housing 102. In other aspects, the power assembly axis 132 may be at any angle perpendicular or parallel to the center axis 120.

Figure 3:
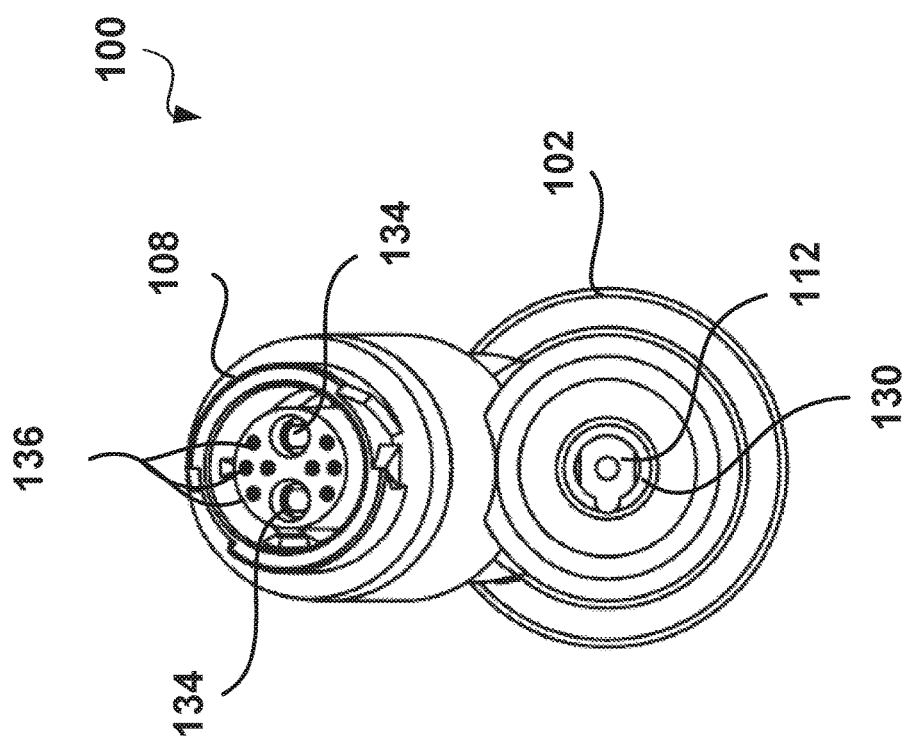
FIG. 3 is a front view of the induction heater assembly of the humidification device of FIG. 1.

FIG. 3 illustrates a front view of an induction heater assembly 100. The power and controls interface assembly 108 may have a plurality of electrical contacts 134 to engage a power source (not shown). The electrical contacts 134 may provide electrical power to the thermocouple contacts 128. The power and controls interface assembly 108 may also include a plurality of electrical pins 136. The electrical pins 136 may be used to facilitate an electrical connection with a power source and/or control interface.

Figure 4:
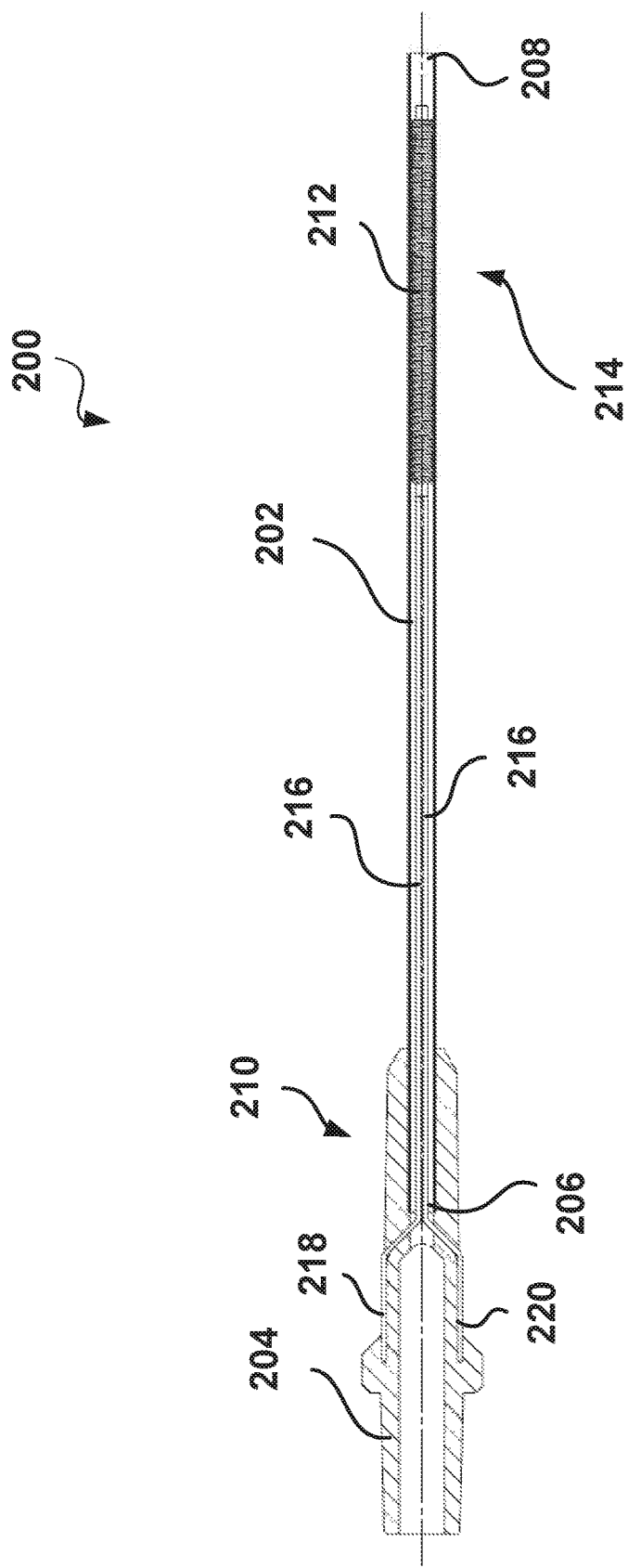
FIG. 4 is a cross-sectional view of a disposable assembly of the humidification device according to an aspect of the invention.

FIG. 4 illustrates a disposable assembly 200 that forms part of a humidification device. The disposable assembly 200 includes a cannula 202 connected to a hub 204. The cannula may be a tube configured to be removably received within the non-magnetic tube 130 and/or housing lumen 112 of the induction heater assembly 100. The cannula 202 may be made from materials such as stainless steel, glass, ceramic, or other suitable materials. The cannula 202 may be magnetic or non-magnetic. The cannula 202 may extend between a proximal end 206 and a distal end 208. The proximal end 206 may be connected to the hub 204 while the distal end 208 may be configured to be inserted into the housing lumen 112 of the induction heater assembly 100. The hub 204 may be formed around a portion of cannula 202 in an overlapping region 210. The hub 204 may have a standardized Luer connection or a custom connection.

The disposable assembly 200 may include a heating element 212 located within the cannula 202. The heating element 212 may be made from a magnetic material such as 1, Alumel, nickel, or other materials with a high relative magnetic permeability. The heating element 212 may be a tube, a solid cylinder such as a rod or wire, a matrix of cylinders, a sintered cylinder, a porous cylinder, a sheet, a spiral sheet, a coil, or any combination of the foregoing. As illustrated in FIG. 4, the heating element 212 may be a twisted or helical coil of multiple wires. The heating element 212 may be located at a distal region 214 of the cannula. In other aspects, the heating element 212 may extend from the proximal end 206 to the distal end 208.

The heating element 212 may be configured to overlap with the induction element 114 when the disposable assembly 200 is removably received within the induction heater assembly 100. The heating element 212 may be configured to interact with the oscillating magnetic field generated by the induction element 114. The heating element 212 can have a high magnetic permeability because the efficiency of induction heating within the heating element 212 may be greater. The heating element 212 can have a greater surface area to increase the efficiency of heat transfer between the fluid pumped into the humidification device and the heating element 212.

The disposable assembly 200 may include thermocouples conductors 216. The thermocouple conductors 216 may allow a user to monitor and/or provide closed-loop temperature control of the heating element 212. The thermocouple conductors 216 may be integrated with the heating element 212 as a single component. In other aspects, the thermocouple conductors 216 may be a separate component from the heating element 212. As illustrated in FIG. 4, the thermocouple conductors 216 are separate components form the heating element 212 with the heating element 212 located at the distal region 214 of the thermocouple conductors 216. In other aspects, one of the thermocouple conductors 216 may be integrated into the cannula 202 and/or be placed in contact with the fluid path, which may allow the cannula 202 and/or a fluid to act as a conductor, such that at least a portion of the measured thermocouple voltage is measured across the cannula 202 and/or fluid.

One or both of the thermocouple conductors 216 may be made from a magnetic material, such as Mu-metal, Alumel, iron, or another alloy, to allow the thermocouple conductors 216 to interact with the oscillating magnetic field generated by the induction element 114 and produce heat, which increases the efficiency of the heating element 212. The thermocouple conductors 216 may be made from the same material as the heating element 212 to simplify fabrication of the disposable assembly 200. In other aspects, at least one of the thermocouple conductors 216 may be made from a non-magnetic alloy to reduce generation of induction heating within the non-magnetic leg and improve accuracy of the temperature measurements. Non-magnetic materials may include copper, Nicrosil, Nisil, Chromel, Constantan, or other similar alloys. A material with low thermal conductivity for the non-magnetic leg can further improve accuracy.

The thermocouple conductors 216 may correspond to a positive electrode and a negative electrode. The voltage differential between the thermocouple conductors 216 may vary depending on the temperature, which may be used to determine and control the temperature of the disposable assembly 200. The thermocouple conductors 216 may have exposed thermocouple conductor surfaces 218 and 220. The exposed thermocouple conductor surfaces 218 and 220 may be located on a surface the hub 204. The exposed thermocouple conductor surfaces 218 and 220 may be configured to engage the thermocouple electrical contacts 128 on the induction heater assembly 100 once the disposable assembly 200 is received within the housing 102 to allow the voltage to be read.

For operation of the humidification device, the disposable assembly 200 may be inserted into the housing 102 of the induction heater assembly 100. The induction element 114 may be excited to generate an oscillating magnetic field, which may create eddy currents within the heating element 212. The eddy currents generated in the heating element 212 may heat the heating element 212. Water may be pumped into the induction heater assembly 100 at the proximal end 104 and through the cannula 202 of the disposable assembly. As water travels past the heating element 212, the water may rapidly absorb heat and vaporize into steam. As steam forms, the rapid expansion may cause pressurized steam to be injected into a patient's breathing circuit gas line and humidify the gases. The steam pressure may also apply force against the supply water. The process may repeat in a cyclical fashion resulting in steam periodically injected into the patient's breathing circuit. FIG. 6 is schematic diagram which includes a standard respiratory system 400 which includes a ventilator 401 and a patient or patient interface 402, which are fluidly interconnected by respiratory breathing circuit 403, as is well known in the art. In the system 400, an embodiment of the humidification device of the invention, such as induction heater assembly 100, is coupled to the respiratory breathing circuit 403, such that steam is injected into a patient's breathing circuit gas line at some point along the respiratory breathing circuit 403, to thereby humidify the gases flowing therein, and deliver humidified gas to the patient or patient interface 402.

Although FIGS. 2 and 4 show the induction heater assembly 100 and the disposable assembly 200 as separate units, in other aspects, the two may be combined to form a single unit. For example, the heating element 212 and thermocouple conductors 216 may be integrated into the induction heater assembly 100. The combined induction heater assembly 100 and disposable assembly 200 may be designed to be disposable and/or replaceable after a limited number of uses.

FIG. 5 illustrates another implementation of the disposable assembly 300 that forms part of a humidification device according another aspect of the disclosure. The disposable assembly 300 is similarly configured to be removably received within the housing 102 of the induction heater assembly 100. The disposable assembly may include a cannula 302, hub 304, and heating element 312 similar to the aspects described above with respect to FIG. 4. In addition, the disposable assembly 300 may include a check valve 314. The check valve 314 may be a valve that only permits fluid to flow from the proximal end 316 to the distal end 318. The check valve 314 may be implemented with at least one of a ball check valve, a diaphragm check valve, a swing check valve, a stop-check valve, a pneumatic non-return valve, or another similar mechanical valve. The check valve 314 may close the supply of water entering the disposable assembly 300 as a result of steam pressure formed within the disposable assembly 300.

While the humidification device has been described in terms of what may be considered to be specific aspects, the disclosure need not be limited to the disclosed aspects. Additional modifications and improvements to the humidification device may be apparent to those skilled in the art. As such, this disclosure is intended to cover various modifications and similar arrangements included within the spirit and scope of the claims, the scope of which should be accorded the broadest interpretation so as to encompass all such modifications and similar structures. The present disclosure is considered as illustrative and not restrictive.

The invention claimed is:

1. A humidification device for a respiratory breathing circuit, comprising:
    an induction heater assembly configured to inject steam into a breathing circuit gas line of the respiratory breathing circuit, the induction heater assembly comprising:
        a housing having a proximal end and a distal end, the housing defining a housing lumen extending from the proximal end to the distal end;
        an induction element located around at least a portion of the housing lumen;
        a power assembly in the housing for connection to a power source;
        a cannula having a proximal end and a distal end, the cannula being disposed within the housing lumen and surrounded by the induction element, the cannula being configured to receive a flow of water;
        a heating element located inside the cannula, the heating element being at least partially surrounded by the induction element; and
        a temperature sensor integrated into the cannula or placed in contact with water flowing within the cannula,
    wherein the induction element is configured to be excited by electrical current supplied from the power assembly, to generate an oscillating magnetic field to create eddy currents in the heating element to heat the heating element, and thereby heat the flow of water in the cannula flowing past the heating element, to thereby vaporize the water into steam which exits the induction heater assembly and housing to be injected into the breathing circuit gas line.

2. The humidification device of claim 1, wherein the heating element includes Mu-metal.

3. The humidification device of claim 1, wherein the heating element includes a magnetic material with a relative magnetic permeability greater than ten thousand.

4. The humidification device of claim 1, wherein the induction element comprises at least one helically wound metallic coil.

5. The humidification device of claim 1, wherein the induction element comprises one or more electrical conductors configured to generate an oscillating magnetic dipole.

6. The humidification device of claim 1, wherein the induction element comprises at least two electrical conductors configured to generate an oscillating magnetic multipole.

7. The humidification device of claim 6, wherein the at least two electrical conductors are wires or a printed circuit.

8. The humidification device of claim 1, wherein the induction heater assembly further comprises a thermal insulator located between the housing and the induction element.

9. The humidification device of claim 1, wherein the induction heater assembly further comprises a non-magnetic tube located within the housing lumen, the non-magnetic tube being disposed around the cannula.

10. The humidification device of claim 1, wherein the housing includes a check valve.

11. The humidification device of claim 1, wherein the power assembly is located at the proximal end of the housing.

12. The humidification device of claim 1, wherein the cannula is made from a material selected from a metal, plastic, glass, ceramic, and a combination thereof.

13. The humidification device of claim 1, wherein the induction heater assembly includes a standardized Luer taper connection for fluid flow into the cannula.

14. The humidification device of claim 1, wherein the induction heater assembly further comprises a plurality of cooling fins radially extending from an exterior surface of the housing.

15. The humidification device of claim 1, wherein the induction heater assembly further comprises a plurality of cooling fins extending into a gas flow line.

16. The humidification device of claim 1, wherein the temperature sensor is a thermocouple that is integrated into the cannula or placed in contact with water flowing within the cannula to act as a conductor such that the thermocouple is configured to measure a temperature across the cannula or the fluid.

* * * * *